(12) United States Patent
Lecomte et al.

(10) Patent No.: US 8,961,618 B2
(45) Date of Patent: Feb. 24, 2015

(54) PROSTHETIC FOOT WITH RESILIENT HEEL

(71) Applicant: Ossur HF, Reykjavik (IS)

(72) Inventors: Christophe Lecomte, Reykjavik (IS);
Marta Bjornsdottir, Reykjavik (IS);
Larus Gunnsteinsson, Reykjavik (IS)

(73) Assignee: Össur hf, Reykjavik (IE)

( * ) Notice: Subject to any disclaimer, the term of this patent is extended or adjusted under 35 U.S.C. 154(b) by 0 days.

(21) Appl. No.: 13/725,494

(22) Filed: Dec. 21, 2012

(65) Prior Publication Data

US 2013/0173023 A1   Jul. 4, 2013

Related U.S. Application Data

(60) Provisional application No. 61/581,580, filed on Dec. 29, 2011.

(51) Int. Cl.
*A61F 2/66* (2006.01)
*A61F 2/68* (2006.01)
*A61F 2/42* (2006.01)
*A61F 2/50* (2006.01)

(52) U.S. Cl.
CPC .................. *A61F 2/4225* (2013.01); *A61F 2/66* (2013.01); *A61F 2002/5007* (2013.01); *A61F 2002/6678* (2013.01)
USPC .............................................. 623/55; 623/53

(58) Field of Classification Search
CPC ....................................................... A61F 2/66
USPC .......................................... 623/27, 29, 53–55
See application file for complete search history.

(56) References Cited

U.S. PATENT DOCUMENTS

| 25,238 A | 8/1859 | Bly |
| 53,931 A | 4/1866 | Weston, et al. |
| 56,983 A | 8/1866 | Nicholas |

(Continued)

FOREIGN PATENT DOCUMENTS

| DE | 1941762 | 3/1971 |
| DE | 2130168 | 1/1973 |

(Continued)

OTHER PUBLICATIONS

The New Flex Foot Assure, The O&P Edge Magazine, Nov. 2008.*

(Continued)

*Primary Examiner* — Thomas J Sweet
*Assistant Examiner* — Christie Bahena
(74) *Attorney, Agent, or Firm* — Knobbe, Martens, Olson & Bear, LLP (57) ABSTRACT

A prosthetic foot can include a resilient heel member that can be removably coupled to the bottom of a plate-like foot member of the prosthetic foot. The heel member can be made of a resilient material, such as foam. The heel member can have a shape that corresponds to a foot cover and allows the prosthetic foot to fit within a foot cover. A lip may be provided to engage with a corresponding portion of the foot cover to secure the heel member within the foot cover. A rib can be located on the bottom of the heel member to create horizontal or vertical displacement of the foot at heel strike. A recess can be created in the heel member to removably receive an insert, which can alter the stiffness of the heel member.

20 Claims, 8 Drawing Sheets

(56) References Cited

U.S. PATENT DOCUMENTS

| | | | |
|---|---|---|---|
| 57,666 A | 9/1866 | Bly | |
| 368,580 A | 8/1887 | Frees | |
| 487,697 A | 12/1892 | Ehle | |
| 534,198 A | 2/1895 | Chapman | |
| 619,731 A | 2/1899 | Doerflinger et al. | |
| 808,296 A | 12/1905 | Merrick | |
| 809,876 A | 1/1906 | Wilkins | |
| 817,340 A | 4/1906 | Rosenkranz | |
| 1,649,773 A | 11/1927 | Witmyer | |
| 2,201,300 A | 5/1938 | Prue | |
| 2,183,076 A | 12/1939 | Kaiser | |
| 2,197,093 A | 4/1940 | Campbell | |
| 2,315,795 A | 4/1943 | Johnson et al. | |
| 2,357,893 A | 9/1944 | Harrington | |
| 2,594,945 A | 4/1952 | Lucas et al. | |
| 2,692,392 A | 10/1954 | Bennington et al. | |
| 2,731,645 A | 1/1956 | Woodall | |
| 3,335,428 A | 8/1967 | Gajdos | |
| 3,551,914 A | 1/1971 | Woodall | |
| 3,784,988 A | 1/1974 | Trumpler | |
| 3,874,004 A | 4/1975 | May | |
| 3,894,437 A | 7/1975 | Hagy | |
| 4,007,497 A | 2/1977 | Haupt | |
| 4,267,728 A | 5/1981 | Manley et al. | |
| 4,360,931 A | 11/1982 | Hampton | |
| 4,387,472 A | 6/1983 | Wilson | |
| 4,416,293 A | 11/1983 | Anderson et al. | |
| 4,547,913 A * | 10/1985 | Phillips | 623/27 |
| 4,631,676 A | 12/1986 | Pugh | |
| 4,652,266 A | 3/1987 | Truesdell | |
| 4,676,801 A | 6/1987 | Lundeen | |
| 4,718,913 A | 1/1988 | Voisin | |
| 4,721,510 A | 1/1988 | Cooper et al. | |
| 4,756,098 A | 7/1988 | Boggia | |
| 4,813,436 A | 3/1989 | Au | |
| 4,814,661 A | 3/1989 | Ratzlaff et al. | |
| 4,822,363 A | 4/1989 | Phillips | |
| 4,858,621 A | 8/1989 | Franks | |
| 4,865,612 A | 9/1989 | Arbogast et al. | |
| 4,892,553 A | 1/1990 | Prahl | |
| 4,892,554 A | 1/1990 | Robinson | |
| 4,959,073 A | 9/1990 | Merlette | |
| 5,019,109 A | 5/1991 | Voisin | |
| 5,037,444 A | 8/1991 | Phillips | |
| 5,062,859 A | 11/1991 | Naeder | |
| 5,066,305 A | 11/1991 | Firth | |
| 5,112,356 A | 5/1992 | Harris et al. | |
| 5,116,384 A | 5/1992 | Wilson et al. | |
| 5,128,880 A | 7/1992 | White | |
| 5,133,778 A | 7/1992 | Dooley, Jr. | |
| 5,139,525 A | 8/1992 | Kristinsson | |
| 5,156,631 A | 10/1992 | Merlette | |
| 5,156,632 A | 10/1992 | Wellershaus | |
| 5,181,932 A | 1/1993 | Phillips | |
| 5,181,933 A | 1/1993 | Phillips | |
| 5,219,365 A | 6/1993 | Sabolich | |
| 5,237,520 A | 8/1993 | White | |
| 5,253,656 A | 10/1993 | Rincoe et al. | |
| 5,258,038 A | 11/1993 | Robinson et al. | |
| 5,258,039 A | 11/1993 | Goh et al. | |
| 5,290,319 A | 3/1994 | Phillips | |
| 5,361,133 A | 11/1994 | Brown et al. | |
| 5,376,133 A | 12/1994 | Gramnas | |
| 5,376,141 A | 12/1994 | Phillips | |
| 5,387,246 A * | 2/1995 | Phillips | 623/56 |
| 5,388,591 A | 2/1995 | DeLuca et al. | |
| 5,405,410 A | 4/1995 | Arbogast et al. | |
| 5,408,873 A | 4/1995 | Schmidt et al. | |
| 5,425,781 A | 6/1995 | Allard et al. | |
| 5,443,522 A | 8/1995 | Hiemisch | |
| 5,443,527 A | 8/1995 | Wilson | |
| 5,443,529 A | 8/1995 | Phillips | |
| 5,471,405 A | 11/1995 | Marsh | |
| 5,474,087 A | 12/1995 | Nashner | |
| 5,509,938 A | 4/1996 | Phillips | |
| 5,545,234 A | 8/1996 | Collier | |
| 5,549,711 A | 8/1996 | Bryant | |
| 5,593,453 A | 1/1997 | Ahlert et al. | |
| 5,623,944 A | 4/1997 | Nashner | |
| 5,653,767 A | 8/1997 | Allen et al. | |
| 5,695,526 A | 12/1997 | Wilson | |
| 5,695,527 A | 12/1997 | Allen | |
| 5,701,686 A | 12/1997 | Berr et al. | |
| 5,728,177 A | 3/1998 | Phillips | |
| 5,753,931 A | 5/1998 | Borchers et al. | |
| 5,766,264 A | 6/1998 | Lundt | |
| 5,769,896 A | 6/1998 | Rosendahl et al. | |
| 5,790,256 A | 8/1998 | Brown et al. | |
| 5,800,569 A | 9/1998 | Phillips | |
| 5,824,112 A | 10/1998 | Phillips | |
| 5,885,229 A | 3/1999 | Yamato et al. | |
| 5,888,239 A | 3/1999 | Wellershaus et al. | |
| 5,897,594 A | 4/1999 | Martin et al. | |
| 5,899,944 A | 5/1999 | Phillips | |
| 5,941,913 A | 8/1999 | Woolnough et al. | |
| 5,944,760 A | 8/1999 | Christensen | |
| 5,957,870 A | 9/1999 | Yamato et al. | |
| 5,957,981 A | 9/1999 | Gramnas | |
| 5,993,488 A | 11/1999 | Phillips | |
| 6,063,046 A | 5/2000 | Allum | |
| 6,071,313 A | 6/2000 | Phillips | |
| 6,099,572 A | 8/2000 | Mosler et al. | |
| 6,115,945 A | 9/2000 | Ellis, III | |
| 6,120,547 A | 9/2000 | Christensen | |
| 6,129,766 A | 10/2000 | Johnson et al. | |
| 6,165,227 A | 12/2000 | Phillips | |
| 6,187,052 B1 | 2/2001 | Molino et al. | |
| 6,197,067 B1 | 3/2001 | Shorter et al. | |
| 6,197,068 B1 | 3/2001 | Christensen | |
| 6,205,230 B1 | 3/2001 | Sundman et al. | |
| 6,206,934 B1 | 3/2001 | Phillips | |
| 6,216,545 B1 | 4/2001 | Taylor | |
| 6,231,527 B1 | 5/2001 | Sol | |
| 6,241,776 B1 | 6/2001 | Christensen | |
| 6,261,324 B1 * | 7/2001 | Merlette | 623/55 |
| 6,280,479 B1 * | 8/2001 | Phillips | 623/52 |
| 6,289,107 B1 | 9/2001 | Borchers et al. | |
| 6,290,730 B1 | 9/2001 | Pitkin et al. | |
| 6,331,893 B1 | 12/2001 | Brown et al. | |
| 6,350,286 B1 | 2/2002 | Atkinson et al. | |
| 6,387,134 B1 | 5/2002 | Parker et al. | |
| 6,398,818 B1 | 6/2002 | Merlette et al. | |
| 6,402,790 B1 | 6/2002 | Celebi | |
| 6,443,993 B1 | 9/2002 | Koniuk | |
| 6,443,995 B1 | 9/2002 | Townsend et al. | |
| 6,546,356 B1 | 4/2003 | Genest | |
| 6,596,029 B1 | 7/2003 | Gramnas | |
| 6,602,295 B1 | 8/2003 | Doddroe et al. | |
| 6,663,672 B1 | 12/2003 | Laghi | |
| 6,663,673 B2 | 12/2003 | Christensen | |
| 6,669,737 B2 | 12/2003 | Mosler et al. | |
| 6,676,708 B1 | 1/2004 | Laghi | |
| 6,699,295 B2 | 3/2004 | Lee et al. | |
| 6,702,859 B1 | 3/2004 | Laghi | |
| 6,702,860 B1 | 3/2004 | Laghi | |
| 6,706,075 B1 | 3/2004 | Laghi | |
| 6,712,860 B2 * | 3/2004 | Rubie et al. | 623/55 |
| 6,718,656 B2 | 4/2004 | Houser et al. | |
| 6,719,807 B2 | 4/2004 | Harris | |
| 6,743,260 B2 | 6/2004 | Townsend et al. | |
| 6,764,521 B2 | 7/2004 | Molino et al. | |
| 6,764,522 B2 | 7/2004 | Cehn | |
| 6,767,370 B1 | 7/2004 | Mosler et al. | |
| 6,793,683 B1 | 9/2004 | Laghi | |
| 6,797,009 B1 | 9/2004 | Laghi | |
| 6,805,717 B2 | 10/2004 | Christensen | |
| 6,807,869 B2 | 10/2004 | Farringdon et al. | |
| 6,811,571 B1 | 11/2004 | Phillips | |
| 6,827,744 B1 | 12/2004 | Laghi | |
| 6,855,170 B2 | 2/2005 | Gramnas | |
| 6,869,451 B1 | 3/2005 | Laghi | |
| 6,875,240 B1 | 4/2005 | Laghi | |
| 6,875,241 B2 | 4/2005 | Christesen | |
| 6,875,242 B2 | 4/2005 | Christensen | |

(56) References Cited

U.S. PATENT DOCUMENTS

| | | |
|---|---|---|
| 6,899,737 B1 | 5/2005 | Phillips |
| 6,929,665 B2 | 8/2005 | Christensen |
| 6,936,074 B2 | 8/2005 | Townsend et al. |
| 6,942,704 B2 | 9/2005 | Sulprizio |
| 6,966,933 B2 | 11/2005 | Christensen |
| 6,969,408 B2 | 11/2005 | Lecomte et al. |
| 7,052,519 B1 | 5/2006 | Gramnas |
| 7,063,727 B2 | 6/2006 | Van Phillips et al. |
| 7,108,723 B2 | 9/2006 | Townsend et al. |
| 7,112,227 B2 | 9/2006 | Doddroe et al. |
| 7,169,190 B2 | 1/2007 | Phillips et al. |
| 7,172,630 B2 | 2/2007 | Christensen |
| 7,181,866 B2 | 2/2007 | Braunschweiler |
| 7,211,115 B2 | 5/2007 | Townsend et al. |
| 7,219,449 B1 | 5/2007 | Hoffberg et al. |
| 7,279,011 B2 | 10/2007 | Phillips |
| 7,318,504 B2 | 1/2008 | Vitale et al. |
| 7,337,680 B2 | 3/2008 | Kantro |
| 7,341,603 B2 | 3/2008 | Christensen |
| 7,347,877 B2 | 3/2008 | Clausen et al. |
| 7,354,456 B2 | 4/2008 | Phillips |
| 7,371,262 B2 | 5/2008 | Lecomte et al. |
| 7,419,509 B2 | 9/2008 | Christensen |
| 7,429,272 B2 | 9/2008 | Townsend et al. |
| 7,431,737 B2 | 10/2008 | Ragnarsdottir et al. |
| 7,462,201 B2 | 12/2008 | Christensen |
| 7,503,937 B2 | 3/2009 | Asgeirsson et al. |
| 7,520,904 B2 | 4/2009 | Christensen |
| 7,531,006 B2 | 5/2009 | Clausen et al. |
| 7,572,299 B2 | 8/2009 | Christensen |
| 7,578,852 B2 | 8/2009 | Townsend et al. |
| 7,581,454 B2 | 9/2009 | Clausen et al. |
| 7,617,068 B2 | 11/2009 | Tadin et al. |
| 7,618,464 B2 | 11/2009 | Christensen |
| 7,637,659 B2 | 12/2009 | Liu et al. |
| 7,637,957 B2 | 12/2009 | Ragnarsdóttir et al. |
| 7,648,533 B2 | 1/2010 | Phillips et al. |
| 7,686,848 B2 | 3/2010 | Christensen |
| 7,727,285 B2 | 6/2010 | Christensen et al. |
| 7,771,488 B2 | 8/2010 | Asgeirsson et al. |
| 7,815,689 B2 | 10/2010 | Bedard et al. |
| 7,833,287 B2 | 11/2010 | Doddroe et al. |
| 7,846,213 B2 | 12/2010 | Lecomte et al. |
| 7,862,621 B2 | 1/2011 | Kloos et al. |
| 7,862,622 B2 | 1/2011 | Dunlap et al. |
| 7,867,285 B2 | 1/2011 | Clausen et al. |
| 7,879,110 B2 | 2/2011 | Phillips |
| 7,891,258 B2 | 2/2011 | Clausen et al. |
| 7,926,363 B2 | 4/2011 | Miller et al. |
| 7,951,101 B2 | 5/2011 | Pusch |
| 7,998,221 B2 | 8/2011 | Lecomte et al. |
| 8,007,544 B2 | 8/2011 | Jonsson |
| 8,025,699 B2 | 9/2011 | Lecomte et al. |
| 8,075,501 B2 | 12/2011 | Miller et al. |
| 8,109,014 B2 | 2/2012 | Miller et al. |
| 8,117,922 B2 | 2/2012 | Xia et al. |
| 8,128,709 B2 | 3/2012 | Thorhallsdottir et al. |
| 8,261,611 B2 | 9/2012 | Kim et al. |
| 8,290,739 B2 | 10/2012 | Tadin et al. |
| 2002/0038522 A1 | 4/2002 | Houser et al. |
| 2002/0040249 A1 | 4/2002 | Phillips |
| 2002/0082713 A1 | 6/2002 | Townsend et al. |
| 2002/0087216 A1 | 7/2002 | Atkinson et al. |
| 2002/0116072 A1 | 8/2002 | Rubie et al. |
| 2002/0128727 A1 | 9/2002 | Merlette et al. |
| 2002/0138923 A1 | 10/2002 | Shaffeeullah |
| 2002/0143408 A1 | 10/2002 | Townsend et al. |
| 2002/0183860 A1 | 12/2002 | Wilkinson et al. |
| 2003/0045944 A1 | 3/2003 | Mosler et al. |
| 2003/0093158 A1 | 5/2003 | Phillips et al. |
| 2003/0120353 A1 | 6/2003 | Christensen |
| 2003/0191540 A1 | 10/2003 | Townsend et al. |
| 2004/0000074 A1 | 1/2004 | Auger et al. |
| 2004/0064195 A1 | 4/2004 | Herr |
| 2004/0068327 A1 | 4/2004 | Christensen |
| 2004/0112138 A1 | 6/2004 | Knirck et al. |
| 2004/0122529 A1 | 6/2004 | Townsend et al. |
| 2004/0162623 A1 | 8/2004 | Phillips |
| 2004/0181289 A1 | 9/2004 | Bedard et al. |
| 2004/0199265 A1 | 10/2004 | Townsend et al. |
| 2004/0225376 A1 | 11/2004 | Townsend et al. |
| 2005/0033450 A1 | 2/2005 | Christensen |
| 2005/0033451 A1 | 2/2005 | Aigner et al. |
| 2005/0038524 A1 | 2/2005 | Jonsson et al. |
| 2005/0038525 A1 | 2/2005 | Doddroe et al. |
| 2005/0060045 A1 | 3/2005 | Smith et al. |
| 2005/0071017 A1 | 3/2005 | Lecomte et al. |
| 2005/0071018 A1 | 3/2005 | Phillips |
| 2005/0097970 A1 | 5/2005 | Nurse |
| 2005/0107889 A1 | 5/2005 | Bedard et al. |
| 2005/0109563 A1 | 5/2005 | Vitale et al. |
| 2005/0137717 A1 | 6/2005 | Gramnäs et al. |
| 2005/0187640 A1 | 8/2005 | Christensen |
| 2005/0203640 A1 | 9/2005 | Christensen |
| 2005/0216097 A1 | 9/2005 | Rifkin |
| 2005/0234563 A1 | 10/2005 | Phillips |
| 2005/0267603 A1 | 12/2005 | Lecomte et al. |
| 2006/0004467 A1 | 1/2006 | Lecomte et al. |
| 2006/0041321 A1 | 2/2006 | Christensen |
| 2006/0069450 A1* | 3/2006 | McCarvill et al. ............... 623/55 |
| 2006/0167563 A1 | 7/2006 | Johnson et al. |
| 2006/0173555 A1 | 8/2006 | Harn et al. |
| 2006/0247794 A1 | 11/2006 | Doddroe et al. |
| 2007/0027557 A1 | 2/2007 | Jonsson et al. |
| 2007/0039205 A1 | 2/2007 | Erb et al. |
| 2007/0043582 A1 | 2/2007 | Peveto et al. |
| 2007/0100465 A1 | 5/2007 | Egan |
| 2007/0106395 A9 | 5/2007 | Clausen et al. |
| 2007/0213840 A1 | 9/2007 | Townsend et al. |
| 2007/0250178 A1 | 10/2007 | Wilson |
| 2007/0255427 A1 | 11/2007 | Kloos et al. |
| 2008/0033578 A1 | 2/2008 | Christensen |
| 2008/0033579 A1 | 2/2008 | Phillips et al. |
| 2008/0046096 A1 | 2/2008 | Bedard et al. |
| 2008/0167730 A1 | 7/2008 | Pusch |
| 2008/0183301 A1 | 7/2008 | Christensen |
| 2008/0188951 A1 | 8/2008 | Christensen et al. |
| 2009/0012630 A1 | 1/2009 | Mosler et al. |
| 2009/0043403 A1* | 2/2009 | Asgeirsson et al. ............ 623/53 |
| 2009/0076626 A1 | 3/2009 | Ochoa |
| 2009/0105845 A1 | 4/2009 | Curtis |
| 2009/0143870 A1 | 6/2009 | Bedard et al. |
| 2009/0204231 A1 | 8/2009 | Bonacini |
| 2009/0222105 A1 | 9/2009 | Clausen |
| 2009/0234463 A1 | 9/2009 | Wilson |
| 2009/0287315 A1* | 11/2009 | Lecomte et al. ................. 623/55 |
| 2009/0293641 A1 | 12/2009 | Clausen et al. |
| 2010/0004757 A1 | 1/2010 | Clausen et al. |
| 2010/0023135 A1 | 1/2010 | Rubie et al. |
| 2010/0030344 A1* | 2/2010 | Hansen et al. .................. 623/53 |
| 2010/0106260 A1 | 4/2010 | Phillips |
| 2010/0324699 A1 | 12/2010 | Herr et al. |
| 2011/0146396 A1 | 6/2011 | Kim et al. |
| 2011/0213471 A1 | 9/2011 | Jónsson |
| 2011/0251520 A1 | 10/2011 | Shieh et al. |
| 2011/0288448 A1 | 11/2011 | Sanders et al. |
| 2011/0320012 A1* | 12/2011 | Christensen et al. ........... 623/55 |
| 2012/0010730 A1 | 1/2012 | Lecomte et al. |
| 2012/0023776 A1 | 2/2012 | Skaja et al. |
| 2012/0035509 A1 | 2/2012 | Wilson et al. |
| 2012/0046760 A1* | 2/2012 | Nissels et al. ................... 623/55 |
| 2012/0151794 A1 | 6/2012 | Hansen et al. |
| 2012/0166091 A1 | 6/2012 | Kim et al. |

FOREIGN PATENT DOCUMENTS

| | | |
|---|---|---|
| EP | 0401864 | 9/1989 |
| EP | 0940129 | 11/1992 |
| EP | 1149568 | 10/2001 |
| FR | 2658717 | 8/1991 |
| GB | 117547 | 8/1918 |
| GB | 120462 | 11/1918 |
| GB | 621576 | 4/1949 |
| GB | 625528 | 6/1949 |

(56) References Cited

FOREIGN PATENT DOCUMENTS

| | | |
|---|---|---|
| GB | 1371996 | 10/1974 |
| KR | 20010055393 | 7/2001 |
| KR | 2002-0041137 | 6/2002 |
| WO | WO8806431 | 9/1988 |
| WO | WO9304645 | 3/1993 |
| WO | WO9418914 | 9/1994 |
| WO | WO9604869 | 2/1996 |
| WO | WO9853769 | 12/1998 |
| WO | WO9952476 | 10/1999 |
| WO | WO0027317 | 5/2000 |
| WO | WO0202034 | 1/2002 |
| WO | WO0228326 | 4/2002 |
| WO | WO02051342 | 7/2002 |
| WO | WO2004032809 | 4/2004 |
| WO | WO2004093959 | 4/2004 |
| WO | WO2005018495 | 8/2004 |
| WO | WO2005041819 | 10/2004 |
| WO | WO2005048887 | 6/2005 |

OTHER PUBLICATIONS

Ibex Foot System Instructions, Mar. 2010, p. 10.*
Lecomte, C., et al., Height-Adjustable Threaded Shock Absorbing Module and Associated Coupling Member, U.S. Appl. No. 13/149,118, filed May 31, 2011.
U.S. Appl. No. 10/987,940, filed Nov. 12, 2004, and its prosecution history, including without limitation, Office Actions, Amendment, Remarks, and any other potentially relevant documents.
U.S. Appl. No. 12/509,010, filed Jul. 24, 2009, and its prosecution history, including without limitation, Office Actions, Amendment, Remarks, and any other potentially relevant documents.
U.S. Appl. No. 12/509,055, filed Jul. 24, 2009, and its prosecution history, including without limitation, Office Actions, Amendment, Remarks, and any other potentially relevant documents.
U.S. Appl. No. 11/139,009, filed May 26, 2005, and its prosecution history, including without limitation, Office Actions, Amendment, Remarks, and any other potentially relevant documents.
U.S. Appl. No. 12/410,147, filed Mar. 24, 2009, and its prosecution history, including without limitation, Office Actions, Amendment, Remarks, and any other potentially relevant documents.
Commercial Ad for College Park Venture Prosthetic Foot; http://www.college/park.com/assets/pdf/VentureInfoSheets.pdf, © 2003, and www.colleue/park.com/CPStore/ProductInfoVenture.asp; available before Aug. 15, 2003.
Endolite Aqualimb product catalog page, http://www.endolite.com/pdfs/products/FeetAqualimb_catpage.pdf, Mar. 2010, believed to have been available before May 26, 2004.
Freedom Innovations FS2000 LP product; http://www.freedom/innovations.com/html/details.html, © 2003; available before Aug. 15, 2003.
Freedom Innovations Runway product; http://www.fredom/innovations.com/product_details.asp?seriesid=2&prodid=11, © 2004; available before Dec. 18, 2003.
Hosmer Dorrance Corporation: The Quantum Foot (4 pages) (no date but published more than one year prior to Nov. 12, 2004).
Kim De Roy, "Influence of alignment variations of a prosthetic foot on lower limb kinematics and plantar pressure during below knee amputee gait," available before Sep. 20, 2004 (with English Abstract).
Ohio Willow Wood Company: Carbon Copy System III brochure, 5 pages; believed to have been available prior to May, 2004.
Ossur Allurion product; http://www.ossur.com/template1.asp?pageid=84 and product catelog pp. 146/149; available before Aug. 15, 2003.
Ossur Elation product; http://www.ossur.com/template1.asp?pageid=263 and product catelog pp. 193/196; available before Aug. 15, 2003.
Ossur Total Concept product, Ossur Product Catalog 2001/2002, pp. 243/249.
Otto Bock, Axtion product; http://www.ottobockus.com/products/lower_limb_prosthetics/axtion.asp; believed to have been released May 2004.
The Quantum Foot (Hosmer Dorrace Corporation), no date but published more than one year prior to Nov. 12, 2004.
PCT/US2005/018737 Search Report (Apr. 5, 2006) filed May 27, 2005.
SE 9400380/3 A (Gernhardsson), published Aug. 5, 1995.
IPOS, DE29912832U1, published Nov. 2000.
KR 2000-002059A notification date of Jan. 15, 2000.
EP 05753573.4 Office Action (Dec. 6, 2012) filed May 27, 2005.
International Search Report dated May 27, 2005 for PCT/US2004/025554 filed Aug. 6, 2004.
International Search Report dated Apr. 28, 2006 for PCT/US2005/017884 filed May 20, 2006.

* cited by examiner

PROSTHETIC FOOT WITH RESILIENT HEEL

CROSS-REFERENCE TO RELATED APPLICATIONS

This application claims the benefit of U.S. Provisional Patent Application No. 61/581,580, entitled "Prosthetic Foot with Resilient Heel for Low Activity Users," and filed Dec. 29, 2011, the entire contents of which are incorporated herein by reference and should be considered part of this specification.

BACKGROUND

1. Field

The present application relates, in certain embodiments, to prosthetic devices. In particular, certain embodiments of the present application relate to a prosthetic foot with a resilient heel.

2. Description of the Related Art

Prosthetic feet of different designs are well known in the art. The various conventional designs have sought to solve various limitations associated with prosthetic feet.

Some prosthetic foot designs employ support members located in the heel region of the prosthetic foot; however, such support members fail to provide adequate cushioning, stability, and balance for the user. Such support members also tend to be heavy or bulky.

Accordingly, there is a need for a heel member that allows for improved cushioning at heel strike, while also aiding in stability and balance. There is also a need for a heel member that provides a more natural gait. Various embodiments disclosed herein address at least some of these shortcomings.

SUMMARY

In accordance with one embodiment, a prosthetic foot with a heel member is provided to improve cushioning, stability, and balance during ambulation. The prosthetic foot can have a lightweight heel member that enables a more natural gait for low activity users. Some embodiments are well-suited for high activity users. Some embodiments provide a desirable shape but are not lightweight.

Several embodiments include a prosthetic foot that has a plate-like foot member. The plate-like foot member can have a proximal portion and a distal portion. The proximal portion can be generally vertical and the distal portion can be generally horizontal. The foot member can have a curved portion between the proximal portion and the distal portion. The curved portion can have a concave upper surface and a convex lower surface. These embodiments can also include an adapter coupled to the proximal portion of the foot member. In these embodiments, the adapter can be generally vertical and configured to couple the proximal portion of the foot member to a prosthetic pylori or socket. These embodiments can also include a resilient heel member coupled to the curved portion of the foot member and disposed below the curved portion of the foot member. The heel member can have a concave front surface coupled to the convex lower surface of the foot member.

Some of the prosthetic foot embodiments include a foot member that has a proximal portion and a distal portion. The embodiments can also include a resilient heel member coupled to the foot member and disposed under the proximal portion of the foot member. The resilient heel member can include a curved front surface coupled to the proximal portion of the foot member; a rear surface facing generally away from the foot member; and a bottom surface. The bottom surface can have at least one rib extending from the bottom surface. Several embodiments include two, three, four, or even more ribs extending from the bottom surface.

In at least one embodiment, a prosthetic foot has a proximal end and a distal end. The prosthetic foot can include a foot member that has a proximal portion and a distal portion. The prosthetic foot can also include a resilient heel member coupled to the foot member and disposed under the proximal portion of the foot member. In several embodiments, the resilient heel member has a rear surface near the proximal end of the prosthetic foot. The rear surface can have a recess. The heel member can have a stiffness. The prosthetic foot can also include a removable insert disposed inside at least a portion of the recess. In some embodiments, the removable insert is configured to alter the stiffness of the heel member. In other embodiments, the removable insert is configured for other purposes.

Several embodiments include a recess that comprises a proximal section, a distal section, and a locking section. The locking section can be disposed between the proximal section and the distal section. The locking section can be narrower than the distal section to facilitate locking the insert inside the heel member. Other embodiments include a recess that does not have a locking section.

At least one embodiment includes an insert that comprises a proximal insert portion, a distal insert portion, and a neck insert portion. The neck insert portion can be disposed between the proximal insert portion and the distal insert portion. The neck insert portion can be narrower than the distal insert portion to facilitate removably coupling the insert to the heel member or to facilitate permanently coupling the insert to the heel member. Other embodiments include an insert that does not have a neck insert portion. Several embodiments include multiple inserts that fit into a single recess. Other embodiments include multiple inserts that fit into multiple recesses. Some embodiments include multiple inserts that couple together to form a neck insert portion.

In one embodiment of the present invention, the prosthetic foot can comprise a plate-like foot member extending from a proximal section to a generally horizontal distal section, the foot member having a curved portion between the proximal and distal sections. The prosthetic foot also comprises an adapter connected to the proximal section of the foot member and configured to removably couple the foot member to a prosthetic pylori or socket. In one embodiment, the adapter may have a cavity configured to receive the proximal end of the foot member. In another embodiment, the adapter may have a hollow portion or a hole to reduce the weight of the adapter. In yet another embodiment of the adapter, the adapter can have a curved rear surface that fits within a recess in the foot member and can be disposed forward of the proximal portion of the foot member. Adhesive or fasteners can be used to secure the adapter to the proximal end of the foot member.

In accordance with one embodiment, a lightweight heel member coupleable to a prosthetic foot is provided. The heel member can be made of a lightweight, resilient material such as foam. In one embodiment, the heel member comprises a front surface, bottom surface, and rear surface. The front surface of the heel member can curve concavely to match the curvature and shape of the prosthetic foot member, allowing the heel member and prosthetic foot to be removeably coupled.

In some instances a user may desire to insert the prosthetic foot into a cosmetic foot cover. Thus, in one embodiment the bottom surface and rear surface of the heel member can be shaped to correspond to the curvature and shape of the inner surfaces of a foot cover, such as Össur's EVO foot cover. Particular embodiments of the heel member may optionally have a lip on a surface of the heel member. The lip can engage with a corresponding lip or overhang portion on an inner surface of a foot cover, thus fixing the heel member and prosthetic foot within the foot cover.

In certain embodiments, the heel member can have at least one rib on the bottom surface to create a horizontal displacement of the foot at heel strike, increasing stability and providing a more natural gait for the user. In certain embodiments, the heel member can have at least one recess configured to removeably receive a wedge insert to increase the stiffness of the heel member. Both the removable wedge insert and the heel member can be made in a variety of stiffnesses (e.g., different durometer foam) to meet the needs of users.

DETAILED DESCRIPTION

An objective of one or more embodiments described below is to provide a prosthetic foot with a lightweight and/or cushioning heel member. In select embodiments, the heel member advantageously provides improved stability and balance, while providing a more natural gait for low activity users. Other embodiments provide only some of these benefits.

Figure 1:
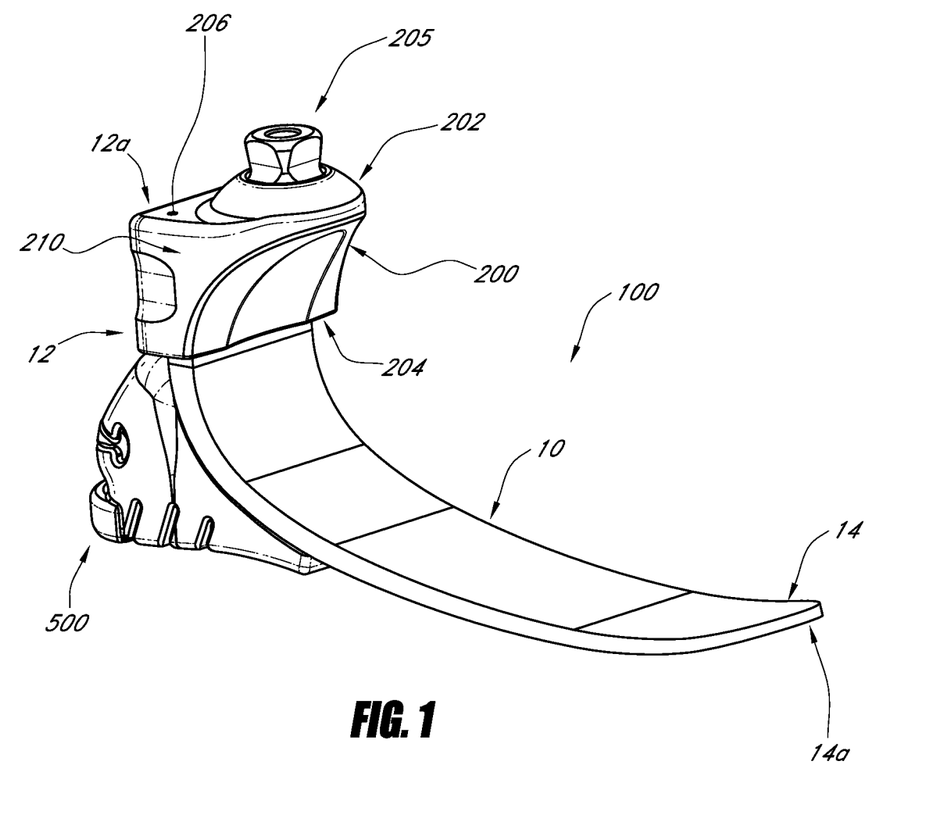
FIG. 1 is a schematic front perspective view of one embodiment of a prosthetic foot coupled with one embodiment of a heel member and one embodiment of an adapter.

FIG. 1 illustrates one embodiment of a prosthetic foot 100 with a resilient heel member 500, which is described further below. The prosthetic foot 100 can have a foot member 10 that extends from a proximal section 12 to a distal section 14. In the illustrated embodiment, the proximal section 12 can be generally vertically oriented (see e.g., FIGS. 1 and 9), and the distal section 12 can be generally horizontally oriented. The foot member 10 can have a curved portion 16 between the proximal section 12 and the distal section 14. The proximal section 12 can extend to a proximal end 12a and can be generally near the location of a natural human ankle. In one embodiment, the distal section 14 can extend to a distal end 14a generally at a location of natural human toes. In another embodiment, the proximal section 12 can be generally inclined with respect to the distal section 14 at an angle other than 90°.

In one embodiment, the foot member 10 is a plate-like member with generally planar top and bottom surfaces and generally rectangular transverse cross-sections. The foot member can be made of lightweight resilient materials, such as one or more of graphite, fiberglass, carbon fiber and the like. In some embodiments, the foot member 10 can be formed of multiple layers of material that define a monolithic piece. In some embodiments, the foot member 10 can have one or more longitudinal slots or splits that extend linearly or in a curved manner toward the front of the foot member 10. In one embodiment, the foot member 10 can have a plurality of such longitudinal splits or slots. In another embodiment, the one or more splits or slots can extend to the front edge of the foot member 10 so as to define separate toe elements.

With continued reference to FIG. 1, the prosthetic foot 100 can have an adapter 200 that attaches to the proximal section 12 of the foot member 10. The adapter 200 extends generally vertically from a proximal end 202 to a distal end 204. The adapter 200 can have a base 210 that is operably coupled to the proximal section 12 of the foot member 10. In one embodiment shown in FIG. 1, the base 210 has a cavity to receive at least a portion of the proximal section 12 of the foot member 10. In one embodiment, the base 210 is attached to the foot member 10 by sliding over the proximal end 12a of the foot member 10. In one embodiment, an adhesive or a bonding agent (e.g., epoxy) can be applied to the proximal section 12 or the interior surfaces of the base 210 to secure the adapter 200 to the proximal section 12 of the foot member 10. For example, an adhesive can be injected into the adapter 200 via an aperture that communicates with the cavity of the base 210, so that the adhesive injected through the aperture flows into the cavity and around the proximal section 12 of the foot member 10. In one embodiment, the adapter 200 can have an aperture 206 as shown in FIG. 1. The aperture 206 can allow air to flow out of the cavity as an adhesive is injected into the adapter 200 or as the adapter 200 is fitted over the proximal section 12 of the foot member 10. In another embodiment, fasteners can be used to secure the adapter 200 to the foot member 10. A connector 205 can be disposed on the proximal end 12a of the adapter 200 for coupling the foot member 10 to a prosthetic pylori or socket. In the illustrated embodiment, the connector 205 is a male pyramid connector. However, in other embodiments the connector 205 can be a tube clamp or other attachment device. In one embodiment the connector 205 can be secured to the adapter 200 with adhesive or a bonding agent. The connector 205 can also be secured to the adapter 200 with fasteners or other hardware. The connector 205 can also be threadably attached to the adapter 200.

Figure 2:
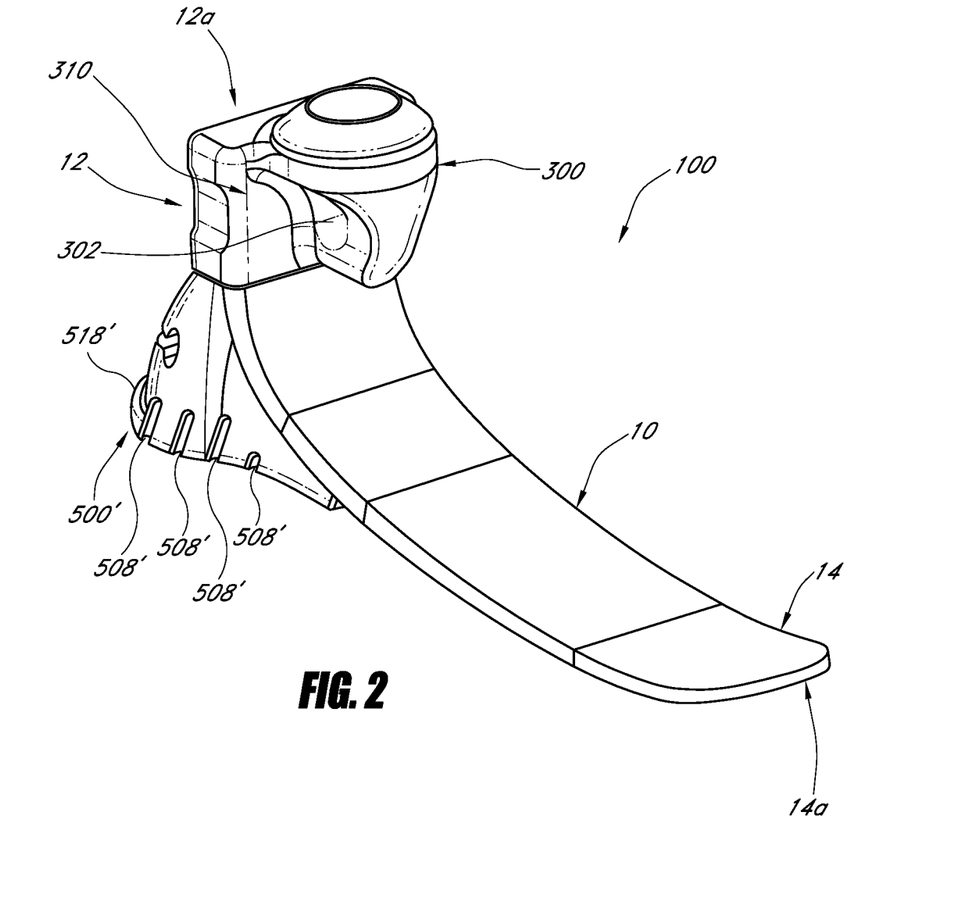
FIG. 2 is a schematic front perspective view of one embodiment of a prosthetic foot coupled with one embodiment of a heel member and another embodiment of an adapter.

FIG. 2 illustrates another embodiment of the prosthetic foot 100. This prosthetic foot is similar to the prosthetic foot pictured in FIG. 1, but with a different embodiment of a heel member 500' and an adapter 300 as noted below. Advantageously, the adapter 300 can have a hole 302 or a hollowed-out portion to reduce the weight of the adapter 300. The adapter 300 is similar to the adapter 200 of FIG. 1 in that the adapter 300 has a cavity for receiving the proximal section 12 of the foot member 10. The adapter 300 can slide over the proximal end 12a of the foot member 10. The adapter 300 can be attached to the proximal section 12 of the foot member 10. An adhesive can be applied to the proximal section 12 or the interior surfaces of the base 310 (e.g., within a cavity defined in the base 310 that fits over the proximal section 12) to further secure the adapter 300 to the proximal section 12 of the foot member 10. Fasteners can also be used to secure the adapter 300 to foot member 10 in other embodiments. Like the adapter 200 of FIG. 1, the adapter 300 can be coupled with a connector 205 to allow the prosthetic foot to connect to a pylori or socket.

Figure 3:
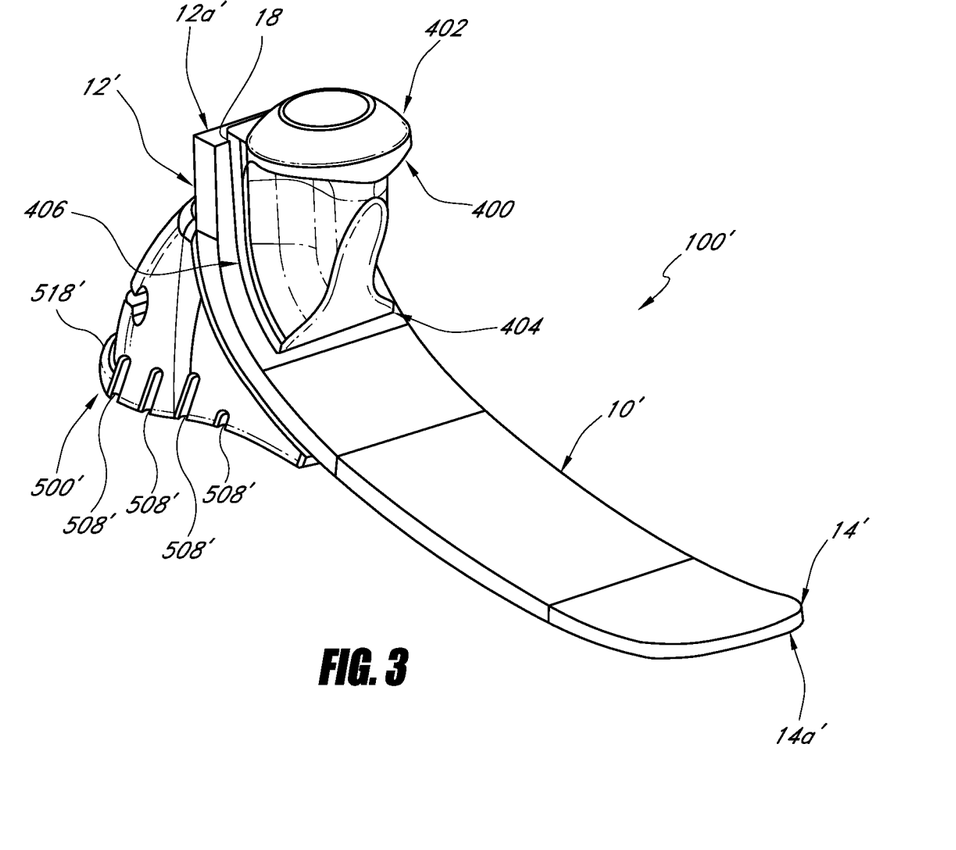
FIG. 3 is a schematic front perspective view of another embodiment of a prosthetic foot coupled with one embodiment of a heel member and another embodiment of an adapter.

FIG. 3 illustrates another embodiment of a prosthetic foot 100' of FIG. 1 with a heel member 500' and yet another embodiment of an adapter 400. The prosthetic foot 100' is similar to the prosthetic foot pictured in FIG. 1, except as noted below. Thus, the reference numerals used to designate the various components of the prosthetic foot 100' are identical to those used for identifying the corresponding components of the prosthetic foot 100 in FIG. 1, except that a "'" has been added to the reference numerals.

In the illustrated embodiment, the adapter 400 extends generally vertically from a proximal end 402 to a distal end 404 and is disposed forwardly of said proximal section 12' of the foot member 10'. In one embodiment, the adapter 400 can have a curvilinear rear surface 406 that corresponds with the curvature of the proximal section 12 of the foot member 10', so at least a portion of the adapter 400 contacts the surface of the proximal section 12 of the foot member 10'. In another embodiment, the foot member 10' may have a recess or slot 18 to slideably receive the adapter 400 and at least partially secure the adapter 400 to the foot member 10'. Adhesive or fasteners can be applied to the contacting surfaces to further secure the adapter 400 to the foot member 10'. In some embodiments, the adapter 400 is press-fit into the recess or slot 18. In other embodiments, the curved rear surface 406 and the recess or slot 18 define a key-slot mechanism for securing the adapter 400 to the foot 100'. Like the adapter 200 of FIG. 1, the adapter 400 can also be coupled with a connector 205 in other embodiments.

Figure 3A:
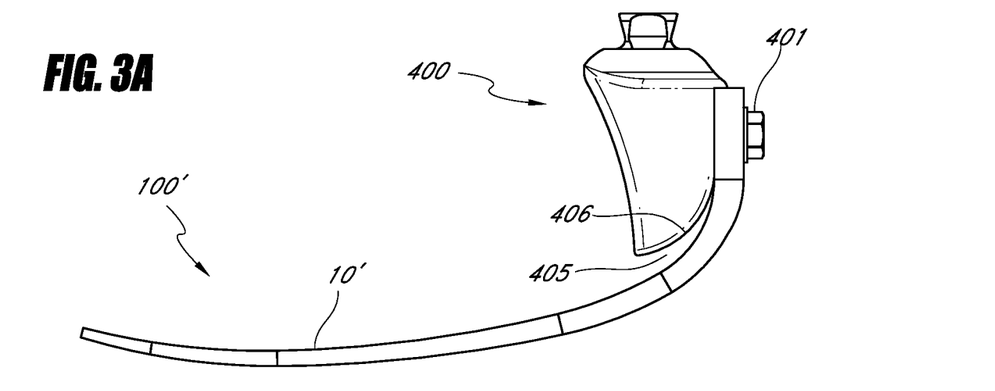
FIG. 3A is a schematic side view of the prosthetic foot of FIG. 3 without the heel member and with a male pyramid on the adapter.
Figure 4:
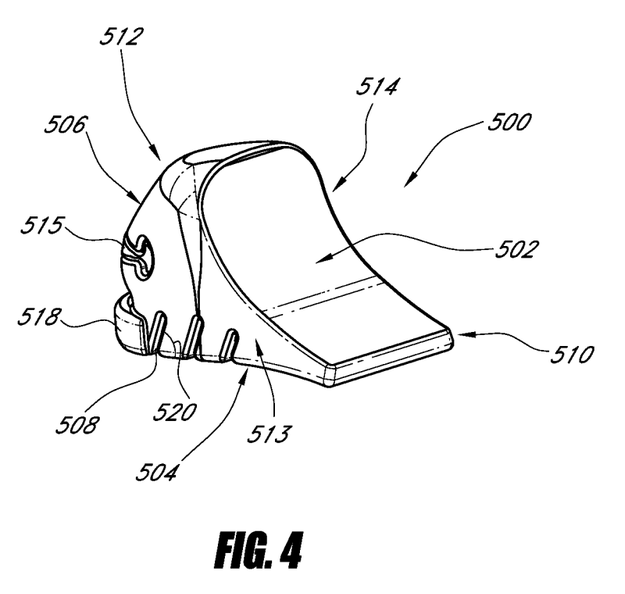
FIG. 4 is a schematic front perspective front view of one embodiment of the heel member in FIG. 1.

As illustrated in FIG. 3A, in one embodiment the adapter 400 can be secured to the proximal section 12' of the prosthetic foot 100' by a fastener 401, such as a bolt. Advantageously, the adapter 400 can be fastened to the foot member 10' with a single fastener 401 (e.g., a single bolt), which reduces the weight of the prosthetic foot and allows for fewer holes to be drilled into the foot member 10'. FIG. 3A also shows that the adapter 400 can be configured so that a bottom portion of the curved rear surface 406 does not contact the foot member 10' when the prosthetic foot 100' is at rest. Thus, the curved rear surface 406 of the adapter 400 and the foot member 100' can define a gap 405 that tapers toward the proximal end 12a' of the foot member 10'. The gap 405 allows the adapter 400 to gradually roll onto the foot plate 10' as the foot moves from heel-strike toward toe-off, thereby gradually increasing the stiffness of the prosthetic foot 100'. However, in other embodiments, there is no gap 405, and the curved rear surface 406 of the adapter 400 can be in contact with the foot plate 10' along the entire length of the adapter 400. The adapter can come in a variety of shapes and configurations, with FIGS. 1-3A illustrating only some possible embodiments.

Further details on prosthetic feet can be found in U.S. Patent Application Publication No. 2011/0213471, filed Feb. 24, 2011, entitled "Prosthetic Foot with a Curved Split"; U.S. Patent Application Publication No. 2005/0137717, filed Dec. 18, 2003, and entitled "Prosthetic Foot with Rocker Member"; U.S. Pat. No. 8,007,544, filed Aug. 15, 2003, and entitled "Low Profile Prosthetic Foot"; U.S. Pat. No. 7,846, 213, filed Nov. 12, 2004, and entitled "Foot Prosthesis with Resilient Multi-Axial Ankle"; and U.S. patent application Ser. No. 13/149,118, filed May 31, 2011, and entitled "Height-adjustable Threaded Shock Absorbing Module and Associated Coupling Member," the entire contents of which are hereby incorporated by reference and should be considered part of this specification. Further details of foot covers and insole portions can be found in U.S. Patent Application Publication No. 2010/0004757, filed Mar. 24, 2009, entitled "Smooth Rollover Insole for Prosthetic Foot" and U.S. Patent Application Publication No. 2006/0015192, filed May 26, 2005, entitled "Functional Foot Cover," the entire contents of which are hereby incorporated by reference and should be considered part of this specification.

FIG. 1 shows a prosthetic foot 100 with one embodiment of a heel member 500 disposed below at least a portion of the foot member 10. FIGS. 2 and 3 show a prosthetic foot 100 with another embodiment of a heel member 500'. Select heel member embodiments provide cushioning, balance, and stability. Various heel member embodiments contribute to a more natural feel for the wearer of the prosthesis. Still other heel member embodiments provide only cushioning.

FIGS. 4-7 further illustrate one embodiment of the resilient heel member 500 shown in FIG. 1. The heel member 500 can be made of many materials, including resilient or elastomeric materials such as one or more of foam (e.g., reticulated foam, expanded polyurethane foam), rubber (e.g., natural rubber, synthetic rubber), plastic, polyurethane, and polypropylene. However, the heel member 500 can be made of other suitable materials, such as other suitable resilient materials, compressible materials, or rigid materials. The heel member 500 can be substantially wedge-shaped in a side elevational aspect, increasing in thickness from a front portion 510 to a rear portion 512. In the illustrated embodiment, the heel member 500 is of a substantially constant width from the medial side 514 to the lateral side 513, although other embodiments have varying widths (e.g., tapered widths).

Figure 9:
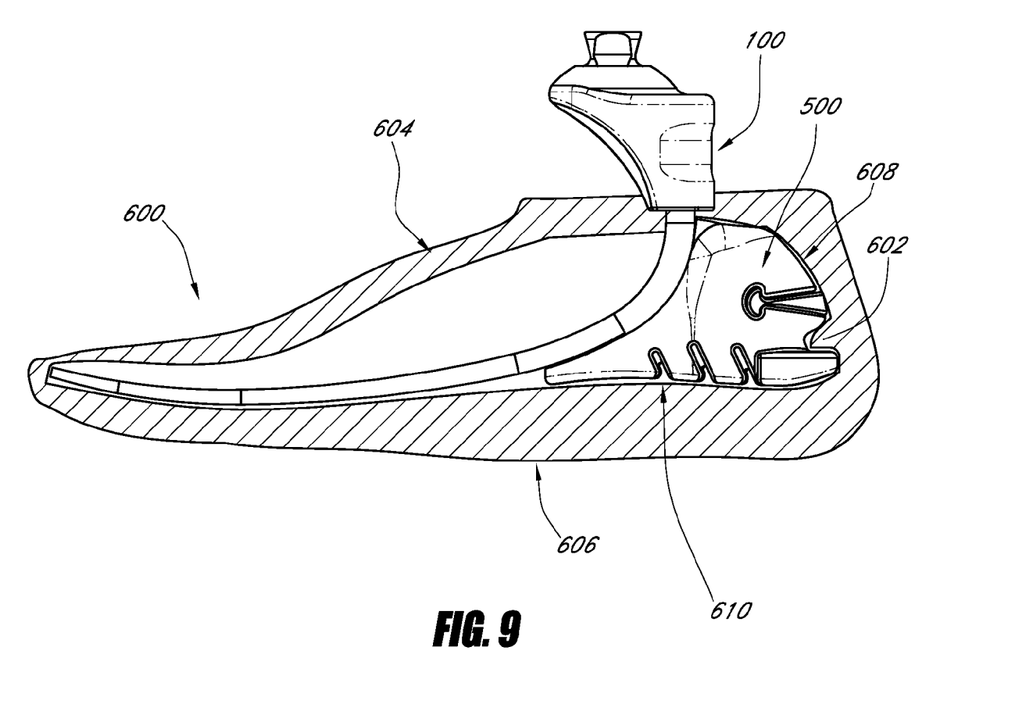
FIG. 9 is a schematic side elevational view of the prosthetic foot of FIG. 1 disposed within one embodiment of a foot cover or cosmesis.

In one embodiment, the shape of the heel member 500 can allow it to be coupled to the foot member 10 and to be placed within a foot cover 600, which is illustrated in FIG. 9. Specifically, the heel member 500 can have a curved front surface 502, bottom surface 504, and rear surface 506. In one embodiment, the front surface 502 can have a concave curvature. The curved front surface 502 can correspond to the curved portion 16 of the foot member 10, allowing the heel member 500 to be removeably coupleable to the foot member 10. In one embodiment, the rear surface 506 can have a convex curvature. The curved rear surface 506 can correspond to the concave shape of a rear inner surface 608 of the foot cover 600. In one embodiment, at least a portion of the bottom surface 504 can have a concave curvature. The curved bottom surface 504 can correspond to the shape of a bottom inner surface 610 of a foot cover 600. Such curvature on the bottom surface 504 of the heel member 500 can also enable the heel member to maintain substantial contact with the bottom inner surface 610 of a foot cover 600 during ambulation from heel-strike to toe-off, which in turn advantageously improves balance, stability, and rollover, which results in improved ease of walking for the wearer of the prosthesis.

In at least one embodiment, the heel member 500 can have a protrusion or lip element 518 at the rear end of the heel member 500. The lip element 518 can be designed to engage with a corresponding lip or overhang structure 602 inside the foot cover 600 to help secure or fix the heel member 500 in place within the foot cover 600. In one embodiment best illustrated in FIGS. 4-6, the lip 518 can extend around the lower edge of the rear surface 506 of the heel member 500. In another embodiment, multiple protrusions or lip elements 518 can be placed at various locations on the heel member 500 to engage with corresponding overhang elements of a foot cover 600.

Figure 5:
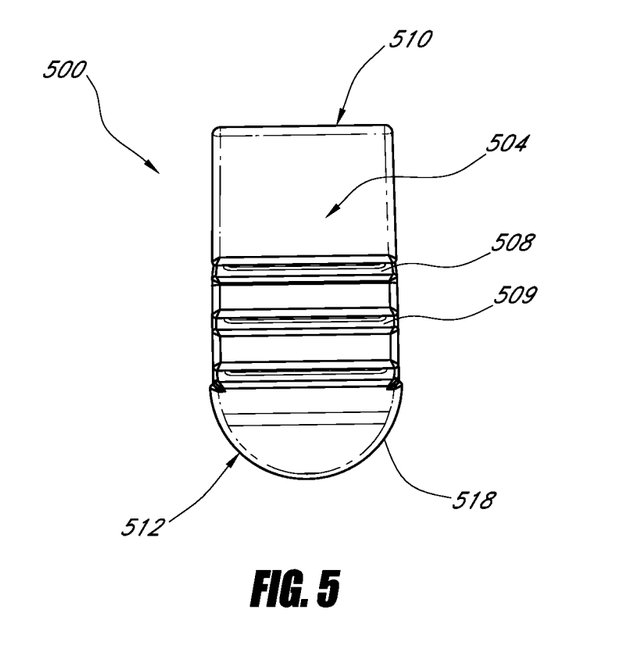
FIG. 5 is a schematic bottom view of the heel member in FIG. 4.
Figure 6:
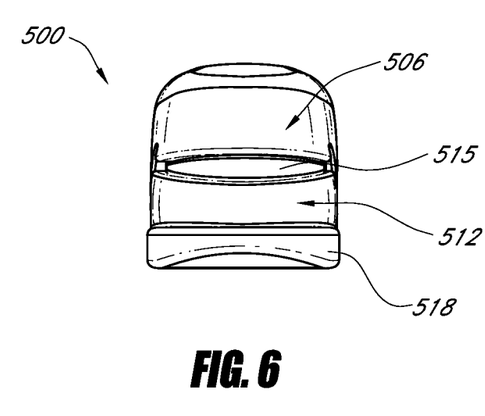
FIG. 6 is a schematic rear elevational view of the heel member in FIG. 4.

In certain embodiments, the heel member 500 can have at least one rib 508 on the bottom surface 504. In the illustrated embodiments, the heel member 500 has a plurality of ribs 508. A rib 508 helps create a horizontal displacement of the prosthetic foot 100 at heel-strike, increasing stability and providing a more natural gait for the user. Additionally, the ribs 508 advantageously help the prosthetic foot transition from heel-strike to plantar-flexion faster, which provides increased stability. In one embodiment, a rib 508 can be arranged to extend across at least a portion of the width of the bottom surface 504. In another embodiment, a rib 508 can extend transversely from the medial side 514 to the lateral side 513 of the heel member 500. In yet another embodiment, a rib 508 can extend partially across the heel member 500, while another rib 508 extends transversely across the heel member 500. In one embodiment with multiple ribs 508 as illustrated in FIG. 5, the ribs are substantially parallel to each other. In one embodiment with multiple ribs 508, the ribs 508 can be of uniform size. In another embodiment with multiple ribs, the ribs 508 can be of varying sizes and shapes, such that adjacent ribs 508 have different depths or widths. A rib 508 can be positioned at any location along the bottom surface 504 of the heel member 500. In one embodiment, the rib 508 may be located approximately in the central region of the bottom surface 504. For example, the embodiment of the heel member 500 illustrated in FIG. 5 has three ribs, wherein the middle rib 509 is located near the approximate central axis of the bottom surface 504 of the heel member 500. Multiple ribs 508 can be spaced a uniform distance apart, or in another embodiment multiple ribs 508 can be spaced various distances from each other. In yet another embodiment, a rib 508 can extend such that an acute angle 520 is formed with respect to the bottom surface 504 of heel member 500.

In certain embodiments, the heel member 500 can have a recess 515. The recess 515 can be configured to receive a removable wedge insert 516 to alter the stiffness of the heel member 500. The removable wedge insert 516 also advantageously provides additional shock absorption in the heel member 500 of the prosthetic foot 100. In one embodiment, the removable wedge insert 516 can be comprised of resilient and compressible material(s), such as foam, rubber, plastic, and the like (e.g., materials similar to those of the heel member 500). Both the removable wedge insert 516 and the heel member 500 can come in a variety of stiffnesses (e.g., different durometer foam) and can be made to have material properties to meet the needs of various users. The density of the removable wedge insert 516 can be selected to fine tune the stiffness of the prosthetic foot 100 to a particular user. In one embodiment, the removable wedge insert 516 can have different material properties than the heel member 500 into which the wedge 516 is inserted. For example, the removable wedge insert 516 may be more or less compressible, or be more or less dense, than the heel member 500 so as to make the heel member 500 less or more stiff.

Figure 7:
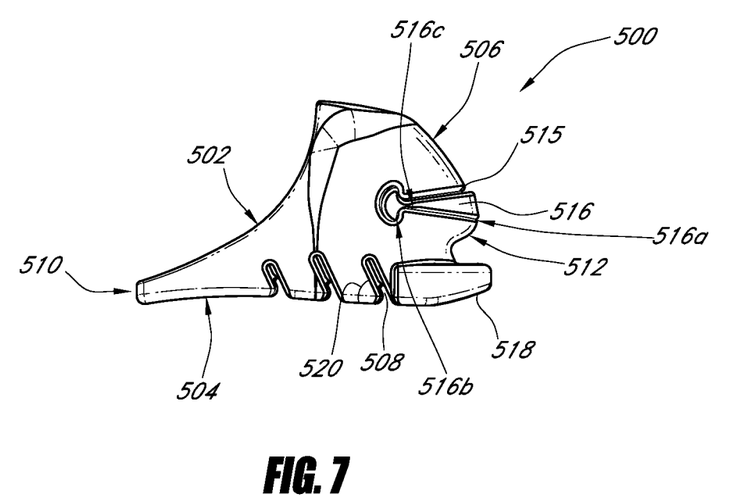
FIG. 7 is a schematic side elevational view of the heel member in FIG. 4.

The recess 515 can be formed in a variety of configurations, shapes, and sizes. In one embodiment as best shown in FIG. 7, the recess 515 opens to the rear surface 506 of the heel member 500. In one embodiment, the recess 515 can extend transversely across the width of the heel member 500 from the medial side 514 to the lateral side 513. In another embodiment, the recess 515 may also be configured to extend only across a portion of the width of the heel member 500. In one embodiment, the recess 515 can extend across the heel member 500 in an orientation substantially perpendicular to a longitudinal axis of the prosthetic foot 100. Additional recesses can be provided in the heel member 500. The additional recesses can be configured to be filled with a removable insert. Further, a recess configured to receive an insert can be positioned at other locations on the heel member 500. As noted above, inserts, such as the insert 516, can be removably inserted into the recess 515 to vary the stiffness of the heel member 500.

In one embodiment, the shape of the recess 515 and the corresponding shape of the wedge 516 can preferably provide for a self-locking system. In one particular embodiment, the recess 515 can have a wedge-shaped section that narrows towards a substantially circular or oval section so as to provide a key hole, as viewed from the side elevational aspect of FIG. 8. In this embodiment, an insert 516 with a corresponding shape, with a wedge-shaped section and a substantially circular section, can fit within the recess 515 and be secured by its shape as shown in FIG. 7. In another embodiment, the recess 515 and corresponding wedge 516 can have any self-locking shape.

FIG. 1 illustrates an embodiment of a prosthetic foot 100 that has a proximal end 12a and a distal end 14a. The foot member 10 has a proximal portion (shown as proximal section 12) and a distal portion (shown as distal section 14). The prosthetic foot 100 has a resilient heel member 500 coupled to the foot member 10 and generally disposed under the proximal portion of the foot member 10.

Referring now to FIG. 7, the resilient heel member 500 comprises a rear surface 506 near the proximal end 12a of the prosthetic foot 100 shown in FIG. 1. The rear surface 506 has a recess 515. The heel member 500 has a stiffness. In some embodiments, the stiffness can be very low to provide extra cushioning. In other embodiments, the stiffness can be very high to provide a firmer feel when the user walks or runs with the prosthetic foot 100.

A removable insert 516 can be disposed inside at least a portion of the recess 515. In some embodiments, the insert is wedge shaped. In other embodiments, the insert is a cube. In yet other embodiments, the insert is a cylinder. In the illustrated embodiment, the insert 516 generally matches the shape of the recess 515. In several embodiments, the insert 516 is configured to alter the stiffness of the resilient heel member 500. For example, inserting an insert 516 that has a higher stiffness than the stiffness of the heel member 500 alters the stiffness by making the heel member 500 stiffer than it would be without the insert 516.

Figure 8:
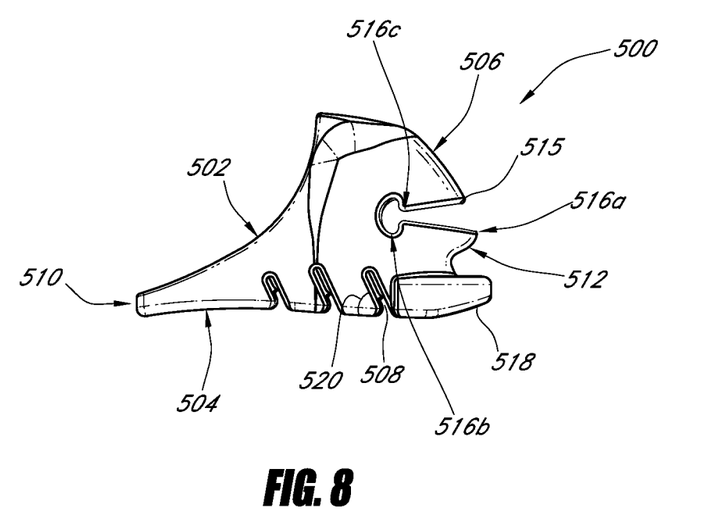
FIG. 8 is another schematic side elevational view of the heel member in FIG. 4.

As explained above, several embodiments have recesses 515 that provide for a self-locking system. In other words, the geometry of the recess 515 helps to hold the insert 516 inside the recess 515 because the shape of the recess 515 and the shape of the insert 516 are such that the insert 516 cannot be pulled out of the recess 515 without displacing the surfaces that define the walls of the recess 515. FIGS. 7 and 8 illustrate an embodiment of a self-locking system. Referring now to FIG. 8, the recess 515 comprises a proximal section 515a, a distal section 515b, and a locking section 515c. The locking section 515c is disposed between the proximal section 515a and the distal section 515b. The locking section 515c is narrower than the distal section 515b to facilitate locking the insert 516 at least partially inside the heel member 500. Various embodiments use different locking section geometries. The example, different embodiments narrow in different directions and locations. A feature that makes a self-locking system is present when the recess has a dimension (such as a width or a height) that is larger deeper inside the recess than the dimension is shallower in the recess. For example, a recess might be 0.5 inches wide deep inside the recess and only 0.2 inches wide less deep inside the recess. This configuration creates a locking feature that interferes with removing the insert 516. Another feature that can make a locking system is geometry that interferes with the insert falling out or being pulled out of the recess.

Referring now to FIG. 7, the insert 516 comprises a proximal insert portion 516a, a distal insert portion 516b, and a neck insert portion 516c. The neck insert portion 516c is disposed between the proximal insert portion 516a and the distal insert portion 516b. The neck insert portion 516c is narrower than the distal insert portion 516b to facilitate removably coupling the insert 516 to the heel member 500. Of note, the proximal section 515a, the distal section 515b, and the locking section 515c of the recess 515 are not labeled in FIG. 7 to enable clearer labeling of the insert 516.

FIGS. 2 and 3 illustrate another embodiment of a heel member 500' attached to foot member 10. The pictured embodiment of the heel member 500' is similar to the embodiment shown in FIGS. 1 and 4-8, except as noted below. The illustrated heel member 500' of FIGS. 2 and 3 has four ribs 508' of varying depths. In one embodiment, the lip 518' can also be smaller. In one embodiment, the heel member 500' can have slightly different curvatures to correspond with a variety of prosthetic foot members and foot covers.

As best illustrated in FIG. 9, in one embodiment, the prosthetic foot 100 with a heel member 500 can be removeably coupled to a foot cover 600 that has an upper portion 604 and a sole portion 606. In one embodiment, the curved rear surface 506 of heel member 500 can correspond to the concave shape of the rear inner surface 608 of the foot cover 600. In one embodiment, the curved bottom surface 504 of heel member 500 can correspond to the shape of the bottom inner surface 610 of the foot cover 600. Such curvature on the bottom surface 504 of the heel member 500 can also enable the heel member to maintain substantial contact with the bottom inner surface of a foot cover 600 as the prosthetic foot moves from heel-strike to toe-off during ambulation. In one embodiment, the heel member 500 can have a lip 518 that engages with a corresponding lip or overhang portion 602 on the inner surface of the foot cover. The lip can help secure the heel member 500 to the foot cover 600. The foot cover 600 generally provides the prosthetic foot 100 with a more anatomical appearance. However, the prosthetic foot 100 is fully functional on its own and may be used without a foot cover.

Of course, the foregoing description is of certain features, aspects and advantages of the present invention, to which various changes and modifications can be made without departing from the spirit and scope of the present invention. The heel members need not feature all of the objects, advantages, features, and aspects discussed above. Similarly, the prosthetic feet need not feature all of the objects, advantages, features, and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of the specific features and aspects between and among the different embodiments may be made and still fall within the scope of the invention. Accordingly, it should be understood that various features and aspects of the disclosed embodiments can be combined with or substituted for one another in order to form varying modes of the discussed prosthetic feet.

What is claimed is:

1. A prosthetic foot comprising:
a monolithic plate-like foot member having a proximal portion and a distal portion, wherein the proximal portion is generally vertical and the distal portion is generally horizontal, the foot member having a curved portion between the proximal portion and the distal portion, the curved portion having a concave upper surface and a convex lower surface;
an adapter coupled to the proximal portion of the foot member, wherein the adapter is generally vertical and configured to couple the proximal portion of the foot member to a prosthetic pylon or socket;
a resilient heel member coupled to the curved portion of the foot member and disposed below the curved portion of the foot member, wherein the heel member has a concave front surface coupled to the convex lower surface of the foot member; and
wherein a bottom surface of the prosthetic foot comprises a bottom surface of the distal portion of the foot member and a bottom surface of the heel member.

2. The prosthetic foot of claim 1, wherein the lower surface of the curved portion has a curvature and the front surface of the heel member generally matches the curvature of the lower surface of the curved portion.

3. The prosthetic foot of claim 1, wherein the lower surface of the curved portion has a shape, the front surface of the heel member contacts the lower surface of the curved portion in a contact region, and the front surface of the heel member generally matches the shape of the lower surface of the curved portion in the contact region.

4. The prosthetic foot of claim 1, wherein the adapter comprises a male pyramid connector that is generally vertically oriented.

5. The prosthetic foot of claim 1, wherein the heel member comprises a rib that extends from the bottom surface.

6. The prosthetic foot of claim 1, wherein the heel member comprises a rear surface facing generally away from the foot member, wherein the rear surface comprises a recess and the recess comprises a proximal section, a distal section, and a locking section, wherein the locking section is disposed between the proximal section and the distal section, and wherein the locking section is narrower than the distal section such that the recess is configured to removably lock an insert at least partially inside the heel member.

7. A prosthetic foot comprising: a monolithic plate-like foot member having a proximal portion, wherein the proximal portion is generally vertical, and a distal portion; and a resilient heel member coupled to the foot member and disposed under the proximal portion of the foot member, the resilient heel member comprising: a curved front surface coupled to the proximal portion of the foot member; a rear surface facing generally away from the foot member; and a bottom surface, wherein the bottom surface has at least two slots extending upward from the bottom surface of the heel member to define a rib, wherein the rib is configured to facilitate the transition from heel-strike to plantar-flexion; wherein a bottom surface of the prosthetic foot comprises a bottom surface of the distal portion of the foot member and the bottom surface of the heel member.

8. The prosthetic foot of claim 7, wherein the foot member comprises a curved portion between the proximal portion and the distal portion, the curved portion having a convex lower surface, the front surface of the heel member is generally concave, and the convex lower surface of the curved portion is coupled to the generally concave front surface of the heel member.

9. The prosthetic foot of claim 8, wherein the convex lower surface of the curved portion generally matches the concave front surface of the heel member.

10. The prosthetic foot of claim 7, wherein the heel member comprises two ribs extending from the bottom surface.

11. The prosthetic foot of claim 10, wherein the two ribs are substantially parallel to each other.

12. The prosthetic foot of claim 7, wherein the heel member has a first rib and a second rib, the first rib has a first shape, the second rib has a second shape, and the first shape is different from the second shape.

13. The prosthetic foot of claim 7, wherein the rib extends from the bottom surface at an acute angle with respect to the bottom surface.

14. The prosthetic foot of claim 7, wherein the heel member has a medial side and a lateral side, and wherein the rib extends from the medial side to the lateral side.

15. The prosthetic foot of claim 7, wherein the rear surface of the heel member comprises a lip that protrudes from the rear surface, wherein the lip is configured to engage a corresponding structure inside a foot cover to removably secure the foot cover to the prosthetic foot.

16. The prosthetic foot of claim 7, wherein the bottom surface of the heel member has a concave curvature.

17. A prosthetic foot comprising:
a plate-like foot member having a proximal portion and a distal portion, wherein the proximal portion is generally vertical and the distal portion is generally horizontal, the foot member having a curved portion between the proximal portion and the distal portion, the curved portion having a concave upper surface and a convex lower surface;
an adapter coupled to the proximal portion of the foot member, wherein the adapter is generally vertical and configured to couple the proximal portion of the foot member to a prosthetic pylon or socket; and
a resilient heel member coupled to the curved portion of the foot member and disposed below the curved portion of the foot member, wherein the heel member has a concave front surface coupled to the convex lower surface of the foot member, wherein the heel member has a top surface coupled to the proximal portion, wherein the heel member has a convex rear surface extending from the top surface.

18. The prosthetic foot of claim 17, wherein the heel member comprises a lip below the convex rear surface, wherein the lip is configured to engage a corresponding structure inside a foot cover to removably secure the foot cover to the prosthetic foot.

19. The prosthetic foot of claim 18, wherein the convex rear surface of the heel member has a curvature that corresponds to an inner concave surface of the foot cover.

20. The prosthetic foot of claim 17, wherein the convex rear surface extends rearward, beyond the proximal portion of the foot member.

* * * * *

UNITED STATES PATENT AND TRADEMARK OFFICE
CERTIFICATE OF CORRECTION

PATENT NO.       : 8,961,618 B2
APPLICATION NO.  : 13/725494
DATED            : February 24, 2015
INVENTOR(S)      : Lecomte Page 1 of 1

It is certified that error appears in the above-identified patent and that said Letters Patent is hereby corrected as shown below:

On the title page item [56]

Column 2 (page 4) line 1, change "colleue" to --college--.

In the specification

Column 1 line 56, Change "pylori" to --pylon--.

Column 2 line 47, Change "pylori" to --pylon--.

Column 4 line 45, Change "pylori" to --pylon--.

Column 5 line 5, Change "pylori" to --pylon--.

Signed and Sealed this
Third Day of November, 2015

Michelle K. Lee
*Director of the United States Patent and Trademark Office*